United States Patent
Lantzsch et al.

(10) Patent No.: US 7,358,387 B2
(45) Date of Patent: Apr. 15, 2008

(54) METHOD FOR PRODUCING 2-DIHALOACYL-3-AMINO-ACRYLIC ACID ESTERS AND 3-DIHALOMETHYL PYRAZOLE-4-CARBOXYLIC ACID ESTERS

(75) Inventors: Reinhard Lantzsch, Wuppertal (DE); Wolfgang Jörges, Odenthal (DE); Sergiy Pazenok, Solingen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/576,059

(22) PCT Filed: Oct. 12, 2004

(86) PCT No.: PCT/EP2004/011376

§ 371 (c)(1), (2), (4) Date: Jun. 29, 2006

(87) PCT Pub. No.: WO2005/042468

PCT Pub. Date: May 12, 2005

(65) Prior Publication Data

US 2006/0252944 A1    Nov. 9, 2006

(30) Foreign Application Priority Data

Oct. 23, 2003    (DE) ................. 103 49 500

(51) Int. Cl.
  *C07C 229/00*    (2006.01)
(52) U.S. Cl. .................................... 560/170
(58) Field of Classification Search ............... 560/170
See application file for complete search history.

(56) References Cited

U.S. PATENT DOCUMENTS

| | | | |
|---|---|---|---|
| 5,498,624 A | 3/1996 | McLoughlin et al. | 514/406 |
| 6,207,828 B1 | 3/2001 | Osei-Gyimah | 544/56 |
| 6,388,124 B2 * | 5/2002 | Takahashi et al. | 560/219 |
| 6,706,911 B1 | 3/2004 | Lui et al. | 560/219 |

OTHER PUBLICATIONS

Angelov, Plamen A., Synthesis of Unsymmetricl Beta-Enamino Kentones, Sep. 24, 2003, Synthesis, vol. 14, pp. 2221-2225.*
Tetrahedron Lett., vol. 37, No. 48, (month unavailable) 1996, pp. 8751-8754, Romuald Bartnik et al, "A New Synthesis of Enaminoketones".
J. Org. Chem., 33, (month unabailable) 1968, p. 816-819, D.C. England et al, "Fluoroketenes. II. Difluoroketene".
J. Het. Chem. 24, May-Jun. 1987, p. 693-695, James R. Beck et al, "Synthesis of 1(1- 1-Dimethylethyl)1-*H*-pyrazole-4-carboxylate Ester Derivatives".

James R. Beck et al: "Synthesis of 1-Aryl-5-(trifluoromethyl)-1H-pyrazole-4-carboxylic Acids and Esters" Journal of Heterocyclic Chemistry, Heterocorporation. Provo, US, Bd. 24, Nr. 3. Mai 1987, Seiten 739-740, XP002126047.

* cited by examiner

*Primary Examiner*—Shaojia Anna Jiang
*Assistant Examiner*—Jennifer Y Cho
(74) *Attorney, Agent, or Firm*—Richard E. L. Henderson

(57) ABSTRACT

The present invention relates to a process for preparing 2-dihaloacyl-3-aminoacrylic esters of the formula (I)

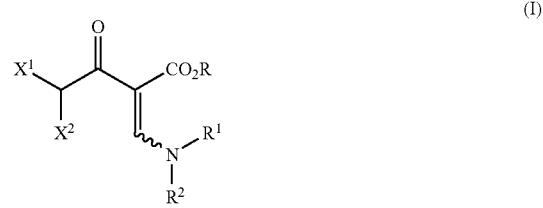

by reacting
acid halides of the formula (II)

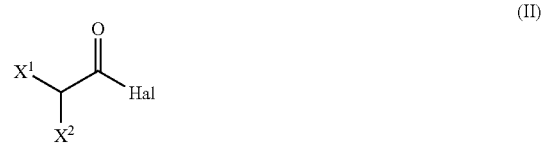

with dialkylaminoacrylic esters of the formula (III)

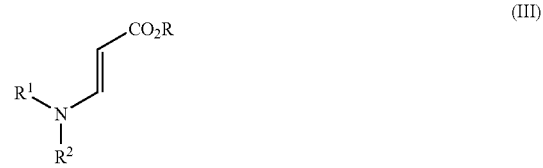

in which R, $R^1$, $R^2$, $X^1$, $X^2$ and Hal are each as defined in the disclosure in a water-immiscible organic solvent in the presence of a base, to the novel 2-dihaloacyl-3-aminoacrylic esters of the formula (I) themselves, to their use for preparing 3-dihalomethylpyrazoles, to a process for preparing 3-dihalo-methylpyrazoles, and to novel 3-dihalomethylpyrazoles.

2 Claims, No Drawings

METHOD FOR PRODUCING 2-DIHALOACYL-3-AMINO-ACRYLIC ACID ESTERS AND 3-DIHALOMETHYL PYRAZOLE-4-CARBOXYLIC ACID ESTERS

The present patent application has been filed under 35 U.S.C. 371 as a national stage application of PCT/EP2004/011376, filed Oct. 12, 2004, which was published in German as International Patent Publication WO 2005/042468 on May 12, 2005, and is entitled to the right of priority of German Patent Application 10349500.2, filed Oct. 23, 2003.

The present invention relates to a novel process for preparing novel 2-dihaloacyl-3-aminoacrylic esters by reacting acid halides with dialkylaminoacrylic esters, to their use for preparing 3-dihalomethylpyrazoles, to a process for preparing 3-dihalomethylpyrazoles, and also to novel 3-dihalomethylpyrazoles.

It is already known that trihaloacylated aminoacrylic esters are obtained when the appropriate chloroacroleins are reacted with a substituted amine. Chloroacroleins required as starting materials are obtained from the corresponding trihaloacetoacetates by means of Vilsmeier reaction. One disadvantage of this process is that phosphorus oxide trichloride has to be used in the Vilsmeier reaction, and another is that the overall yields on the industrial scale are not satisfactory (cf. *Tetrahedron Lett.* 1996, 37, 8751-8754).

It is also known that trihaloacylaminopropenoates are obtained by reacting trihaloacetoacetates with diialkylformamide acetals (cf. EP-A 1 000 926). A disadvantage here is that the deacylated compound occurs as a by-product and has to be removed from the desired product.

It is also known that 2-perhaloacyl-3-aminoacrylic acid derivatives can be obtained by reacting 3-aminoacrylic esters with perhaloalkylcarboxylic anhydrides (cf. WO 03/051820). This process is unsuitable for preparing dihaloacyl-substituted aminoacrylic acid derivatives, since hydrogen chloride is eliminated in the presence of triethylamine when there is an α-hydrogen. The resulting dihaloketenes are very unstable compounds (cf. *J. Org. Chem.* 1968, 33, 816) which tend to polymerize.

3-Difluoromethylpyrazole derivatives can be obtained when 2-(difluoroacetyl)-3-alkoxyacrylates are reacted with hydrazines in protic solvents (cf. U.S. Pat. No. 5,498,624). The yields of this process leave something to be desired, since the undesired isomeric pyrazoles are formed in a high percentage and further losses arise in the isolation of the desired isomer. The industrial application of such a process is therefore barely possible for economic reasons.

In the ring-closing reaction of alkoxy acrylates with hydrazine derivatives, a high percentage (up to 88%) of the undesired 5-haloalkylpyrazole-4-carboxylic acid is formed (cf. *J. Het. Chem.* 1987, 24, 693).

The dihalomethyl alkoxyacrylates are prepared from dihaloacetoacetic esters. Dihaloacetoacetic esters are not available industrially and require complex technology (use of ketene). Such compounds therefore cannot be prepared in an economic manner.

WO 03/051820 discloses that 2-perhaloacyl-3-aminoacrylic acid derivatives can be reacted with hydrazines to give 3-perhalo-substituted pyrazoles. The use of an aprotic solvent reduces the formation of the undesired isomer, but is still considerable in the case of application to the inventive dihalo compounds (Comparative Example 3).

It is thus an object of the present invention to provide novel, economic processes by which 2-dihaloacyl-3-aminoacrylic esters can be obtained with high overall yield and high purity and can be converted with high selectivity to the desired 3-dihalomethylpyrazole-4-carboxylic esters.

The present invention thus provides a process for preparing 2-dihaloacyl-3-aminoacrylic esters of the formula (I)

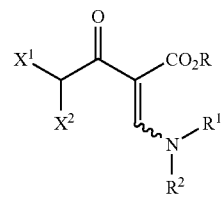

in which
R, $R^1$ and $R^2$ are each independently $C_1$-$C_4$-alkyl and
$X^1$ and $X^2$ are each independently fluorine, chlorine or bromine, characterized in that
a) acid halides of the formula (II)

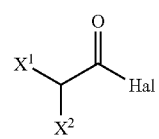

in which
Hal is fluorine, chlorine or bromine and
$X^1$ and $X^2$ are each independently fluorine, chlorine or bromine are reacted with dialkylaminoacrylic esters of the formula (III)

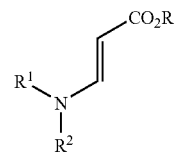

in which R, $R^1$ and $R^2$ are each as defined above in a water-immiscible organic solvent in the presence of a base.

Surprisingly, the 2-dihaloacyl-3-amino-acrylic esters of the formula (I) can be prepared under the inventive conditions with good yields in high purity, whereby the process according to the invention overcomes the abovementioned disadvantages of similar existing preparative processes. In particular, it has been found that, surprisingly, with pyridine or pyridine derivatives, unlike other tertiary amines, for example triethylamine, dihaloketene formation is suppressed and particularly high yields are thus achieved.

When the starting materials used are dichloroacetyl chloride and ethyl dimethylarinoacrylate, and the base used is sodium hydroxide, the process according to the invention (a) can be illustrated by the following scheme.

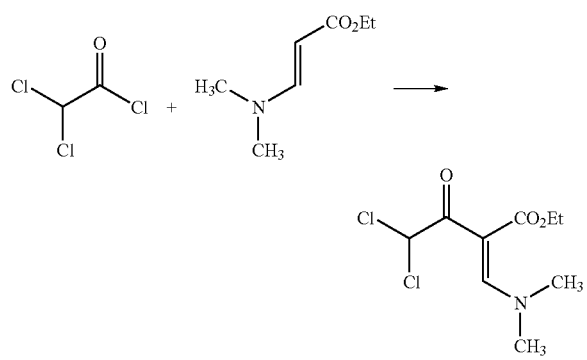

The acid halides used as starting materials when carrying out the process according to the invention (a) are generally defined by the formula (II). In this formula, Hal is preferably fluorine or chlorine, more preferably chlorine. X is preferably fluorine or chlorine.

Acid halides of the formula (II) are known synthesis chemicals.

The dialkylaminoacrylic esters which are also used as starting materials when carrying out the process according to the invention (a) are generally defined by the formula (III). In this formula, R, $R^1$ and $R^2$ are each independently methyl, ethyl, n-propyl or isopropyl. R is more preferably methyl or ethyl; $R^1$ and $R^2$ are more preferably each independently methyl or ethyl, most preferably each methyl.

Dialkylaminoacrylic esters of the formula (III) are known synthesis chemicals.

The process according to the invention (a) is carried out in the presence of a water-immiscible organic solvent. These preferably include aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane. Particular preference is given to using toluene, xylene, chlorobenzene, n-hexane, cyclohexane or methylcyclohexane, very particular preference to toluene or xylene.

The process according to the invention (a) is carried out in the presence of a base. Particularly suitable for this purpose are inorganic aqueous bases, pyridine or pyridine derivatives. Preference is given to using alkaline earth metal or alkali metal hydroxides, carbonates or hydrogencarbonates, for example sodium hydroxide, potassium hydroxide, lithium hydroxide, calcium hydroxide, sodium carbonate, potassium carbonate, potassium hydrogencarbonate or sodium hydrogencarbonate. Particular preference is given to using sodium hydroxide, potassium hydroxide, lithium hydroxide, calcium hydroxide, sodium carbonate or sodium hydrogencarbonate, very particular preference to sodium hydroxide or potassium hydroxide. The inorganic base is preferably used as an aqueous solution in concentrations between 10 and 40%. Also preferably used as bases are pyridine, 2-, 3- or 4-methylpyridine, 2-methyl-5-ethyl-pyridine, 2,4,6-collidine, 2- or 4-n-propylpyridine, 4-dimethylaminopyridine, quinoline or quinaldine, more preferably pyridine, 2-methyl-5-ethylpyridine, 2,4,6-collidine, quinoline or quinaldine.

When carrying out the process according to the invention (a), it is necessary to work within a relatively small temperature range. In general, the working temperatures are −20° C. to +50° C., preferably −10° C. to +30° C.

The process according to the invention (a) is generally carried out under atmospheric pressure. However, it is also possible to work under elevated pressure, for example when the volatile difluoroacetyl fluoride or chloride is used.

The reaction time is not critical and may be selected within a relatively wide range depending on the batch size.

When carrying out the process according to the invention (a), for 1 mol of acid halide of the formula (II), generally between 0.5 mol and 3 mol, preferably between 0.5 mol and 1.5 mol, more preferably between 0.9 mol and 1.0 mol, of a dialkylaminoacrylic ester of the formula (III) are used. The base is generally used in an equimolar amount to the acid halide of the formula (II).

Preference is given to initially charging the acid halide of the formula (II) dissolved in the solvent and adding the dialkylaminoacrylic ester of the formula (III). However, the reverse sequence is also possible. Subsequently, the base used is metered in.

On completion of reaction, the hydrohalide of the pyridine derivative may be brought into solution with water or the aqueous phase present may be removed by phase separation. The 2-dihaloacyl-3-aminoacrylic esters of the formula (I) may be used in the following reaction stage (pyrazole synthesis) without further purification in the remaining organic phase, optionally after drying, for example by incipiently distilling the solvent.

The 2-dihaloacyl-3-aminoacrylic esters of the formula (I) which can be prepared by the process according to the invention (a) are novel and likewise form part of the subject-matter of this application.

2-Dihaloacyl-3-aminoacrylic esters of the formula (I) are valuable intermediates for the preparation of dihalomethyl-substituted pyrazolylcarboxylic acid derivatives which in turn constitute precursors of active fungicidal ingredients (cf. WO 03/070705).

This application therefore likewise provides the use of 2-dihaloacyl-3-aminoacrylic esters of the formula (I) for preparing 3-dihalomethyl-1H-pyrazole-4-carboxylic esters of the formula (V). These esters may optionally be hydrolysed to the acid and optionally derivatized further to the corresponding acid halides. Acid and acid halide may then be converted to fungicidally active carboxamides (cf. WO 03/070705).

The present invention likewise provides a process for preparing 3-dihalomethylpyrazole-4-carboxylic esters of the formula (V)

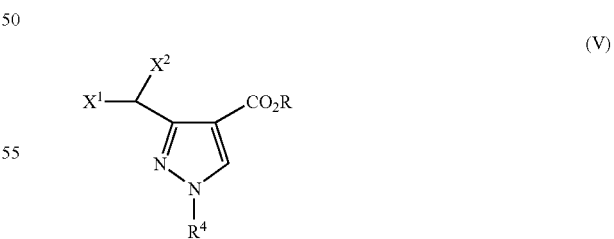

(V)

in which

R is $C_1$-$C_4$-alkyl, $X^1$ and $X^2$ are each independently fluorine, chlorine or bromine, $R^4$ is $C_1$-$C_4$-alkyl, hydroxy-$C_1$-$C_4$-alkyl, $C_2$-$C_6$-alkenyl, $C_3$-$C_6$-cycloalkyl, $C_1$-$C_4$alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio- $C_1$-$C_4$alkyl, $C_1$-$C_4$-haloalkoxy-$C_1$-$C_4$-alkyl having in each case 1 to 5 halogen atoms, or is phenyl, characterized in that b) 2-dihaloacyl-3-aminoacrylic esters of the formula (I)

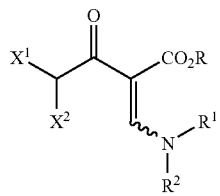

(I)

in which

R, $R^1$ and $R^2$ are each independently $C_1$-$C_4$-alkyl and $X^1$ and $X^2$ are each independently fluorine, chlorine or bromine are reacted with hydrazine derivatives of the formula (IV)

$$R^4\text{—NH—NH}_2 \quad (IV)$$

in which $R^4$ is as defined above at temperatures of −50° C. to 0° C. in the presence of an aprotic solvent.

According to the prior art, 2-dihaloacyl-3-aminoacrylic esters of the formula (I) are typically reacted with hydrazine derivatives in ethanol as a solvent (cf. U.S. Pat. No. 5,498,624). This also gives the incorrect pyrazole isomer (1-methyl-5-difluoromethylpyrazole-4-carboxylic acid) to a considerable extent (correct/incorrect isomer ratio 65:35), which can be removed by distillation. The yield of the desired isomer is only 46.8% of theory. Application of the conditions of WO 03/051820 to the inventive dihalomethyl derivatives likewise only gives an isomer ratio of approx. 68:32 (Comparative Example 3).

It has now been found that, surprisingly, in the reaction of 2-dihaloacyl-3-aminoacrylic esters of the formula (I) with hydrazine derivatives of the formula (IV) (especially with methylhydrazine), the selection of the temperature, the metering and the solvent allows the isomer ratio of desired to undesired pyrazole to be controlled and minimized.

When ethyl 2-(dichloroacetyl)-3-(dimethylamino)acrylate and methylhydrazine are used as starting materials, the progress of the process according to the invention (b) can be illustrated by the following scheme.

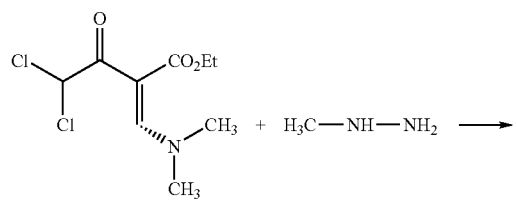

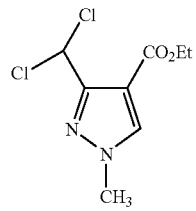

The 2-dihaloacyl-3-aminoacrylic esters of the formula (I) required as starting materials when carrying out the process according to the invention (b) likewise form part of this invention and can be prepared by the process according to the invention (a) (see above).

The hydrazine derivatives which are also required as starting materials when carrying out the process according to the invention (b) are generally defined by the formula (IV). In this formula, $R^4$ is preferably methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl, more preferably methyl, ethyl, isopropyl, n-propyl or tert-butyl, most preferably methyl.

The hydrazine derivatives of the formula (IV) are known synthesis chemicals.

In the process according to the invention (b), the ring closure to the pyrazole is carried out in the presence of an aprotic solvent. These preferably include aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; ketones such as acetone, methyl ethyl ketone, methyl isobutyl ketone or cyclohexanone; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given to using toluene, xylene, chlorobenzene, n-hexane, cyclohexane or methylcyclohexane, very particular preference to toluene or xylene.

In the process according to the invention (b), it is necessary in the ring closure to the pyrazole to work within a relatively small temperature range. The lower the temperature, the better. However, excessively low temperatures are uneconomic from an economic point of view. In general, working temperatures are −50° C. to +20° C., preferably −30° C. to 0° C., more preferably −20° C. to 0° C.

In the process according to the invention (b), the ring closure to the pyrazole is generally carried out under atmospheric pressure. However, it is also possible to work under elevated or reduced pressure.

In the process according to the invention (b), either the 2-dihaloacyl-3-aminoacrylic ester of the formula (I) or the hydrazine derivative can be initially charged in the ring closure to the pyrazole. However, in order to obtain the desired pyrazole derivative in high yield and selectivity, it is advantageous, contrary to the prior art, to initially charge the hydrazine derivative and to meter in the ester of the formula (I).

On completion of reaction, extraction is initially effected with water, the organic phase is removed and the solvent is removed by distillation. The incorrect isomer (1-methyl-5-difluoromethylpyrazole-4-carboxylic acid) can in many cases be removed by crystallization. It is also possible first to hydrolyse to the acid and subsequently to recrystallize.

This invention also provides the overall process for preparing 3-dihalomethyl-1H-pyrazole-4-carboxylic esters of the formula (V), characterized in that 2-dihaloacyl-3-aminoacrylic esters of the formula (I) are first prepared by the process according to the invention (a) and these are reacted further either after isolation or directly, and cyclized with hydrazine derivatives of the formula (IV) in the process according to the invention (b).

Some of the 3-dihalomethyl-1H-pyrazole-4-carboxylic esters obtainable by the process according to the invention (b) are novel. This application likewise provides 3-dihalomethyl-1H-pyrazole-4-carboxylic esters of the formula (V-a)

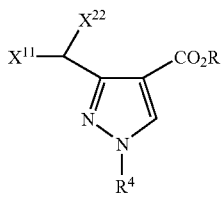

(V-a)

in which
R is $C_1$-$C_4$-alkyl,
$X^{11}$ and $X^{22}$ are each chlorine,
$R^4$ is $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkly, $C_1$-$C_4$-haloalkoxy-$C_1$-$C_4$-alkyl having in each case 1 to 5 halogen atoms, or is phenyl.

The inventive preparation of 2-dihaloacyl-3-aminoacrylic esters of the formula (I), and also their use for preparing dihalomethyl-substituted pyrazole derivatives of the formula (V), are described in the examples which follow, which further illustrate the above description. However, the examples should not be interpreted in a restrictive manner.

PREPARATIVE EXAMPLES

Example 1

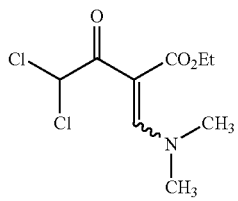

71.6 g (0.5 mol) of ethyl dimethylaminoacrylate are dissolved in 150 ml of toluene and the mixture is cooled to 0° C. Subsequently, 73.7 g (0.5 mol) of dichloroacetyl chloride (dissolved in 50 ml of toluene) are added dropwise at 0-3° C. within 30-40 min with stirring to the solution. Then, at the same temperature, 200 g of 10% sodium hydroxide solution are added dropwise within 20 min, in the course of which a yellow emulsion forms. The mixture is stirrred at 0-3° C. for a further 3 h and allowed to come to room temperature. The phases are separated. The aqueous phase is extracted with 100 ml of toluene and the combined organic phases are washed with 100 ml of water. The toluene phase is dried by incipient distillation and used in the next stage (see Example 4).

The product can be isolated by distilling off the toluene. 101.9 g (80.2% of theory) of ethyl 2-(dichloroacetyl)-3-(dimethylamino)acrylate are obtained.

$^1$H NMR (CD$_3$CN): δ=7.93 (s, 1H), 7.22 (s, 1H), 4.15-4.19 (m, 2H) 3.32(s, 3H), 2.85 (s, 3H), 1.25-1.29 (t, 3H) ppm.

Example 2

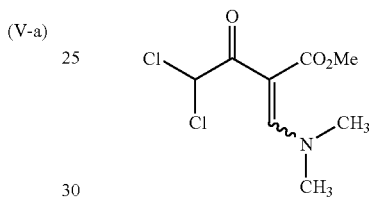

57.6 g of methyl dimethylaminoacrylate are reacted in a similar manner to Example 1 to obtain 95.2 g (79.3% of theory) of methyl 2-(dichloroacetyl)-3-(dimethylamino) acrylate.

Example 3

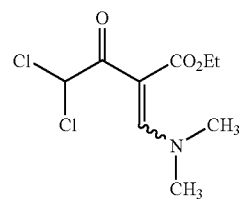

71.6 g (0.5 mol) of ethyl dimethylaminoacrylate are dissolved in 150 ml of toluene and added dropwise with stirring at 0-3° C. to a solution of 73.7 g (0.5 mol) of dichloroacetyl chloride in 50 ml of toluene. Then, at the same temperature, 200 g of 10% sodium hydroxide solution are added dropwise within 20 min, in the course of which a yellow emulsion forms. The mixture is stirred at 0-3° C. for a further 3 h and allowed to come to room temperature. The phases are separated. The aqueous phase is extracted with 100 ml of toluene and the combined organic phases are washed with 100 ml of water. The toluene phase is dried by incipient distillation and used in the next stage (see Example 4).

The product can be isolated by distilling off the toluene. 106.7 g (84% of theory) of ethyl 2-(dichloroacetyl)-3-(dimethylamino)acrylate are obtained.

Example 4

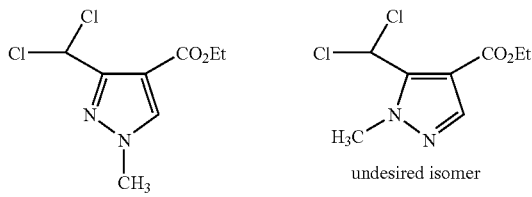

undesired isomer

A solution of 239.3 g of ethyl 2-(dichloroacetyl)-3-(dimethylamino)acrylate in 940 ml of toluene is added dropwise with stirring and under protective gas at 0° C. within 45 min to 44.26 g of methylhydrazine in 940 ml of toluene. The mixture is stirred at 0° C. for 3 h, allowed to come to room temperature and stirred at 20-25° C. for another 2 h. After 200 ml of water have been added, the toluene phase is removed and the water phase extracted twice more with 200 ml each time of toluene. The combined toluene phases are washed with 300 ml of water and incipiently distilled.

Ethyl 3-(dichloromethyl)-1-methyl-1H-pyrazole-4-carboxylate (yield 77.5% of theory) is obtained in a mixture with the undesired isomer [ethyl 5-(dichloromethyl)-1-methyl-1H-pyrazole-4-carboxylate] in a ratio of 81.4:18.6 (GC-MS analysis). The pure ethyl 3-(dichloromethyl)-1-methyl-1H-pyrazole-4-carboxylate melts at 41° C.

Examples 5 to 8 are carried out in a similar manner to Example 4. In each case, the solvent, the reaction temperature and the sequence of the reactants added are varied. Depending on the selection of the reaction conditions, different isomer ratios are obtained. The results of these examples are summarized in the following Table 1.

TABLE 1

| Ex. | Reaction temperature | Solvent | Initial charge | Isomer ratio |
|-----|----------------------|---------|----------------|--------------|
| 5 | −20° C. | Toluene | Methylhydrazine | 87.3:12.7 |
| 6 | +20° C. | Toluene | Methylhydrazine | 69.9:30.1 |
| 7 | +40° C. | Toluene | Methylhydrazine | 61.7:38.3 |
| 8 | 0° C. | Toluene | Ethyl 2-(dichloroacetyl)-3-(dimethylamino)acrylate | 67.9:32.1 |

Example 9

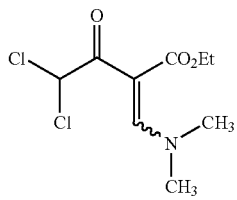

A solution of 14.7 g (0.1 mol) of dichloroacetyl chloride in 25 ml of toluene is added dropwise with stirring at 0° C. to 14.3 g (0.1 mol) of ethyl dimethylaminoacrylate and 9.5 g (0.1 mol) of 98% 2-methylpyridine in 75 ml of toluene. The mixture is allowed to come to room temperature and stirred for a further 30 min. After 100 ml of water have been added, the phases are separated, the aqueous phase is extracted with 50 ml of toluene and the combined organic phases are washed with 50 ml of water. The toluene phase is dried by incipient distillation and used in the next stage (cf. Example 4).

The product can be isolated by distilling off the toluene. 23.2 g (91.3% of theory) of ethyl 2-(dichloroacetyl)-3-(dimethylamino)acrylate (m.p. 71-72° C.) are obtained.

Example 10

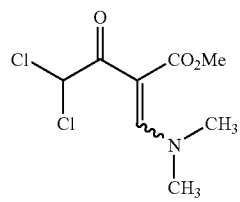

A solution of 7.4 g (0.05 mol) of dichloroacetyl chloride in 15 ml of toluene is added dropwise with stirring at 0° C. to 6.9 g (0.05 mol) of 93% methyl dimethylaminoacrylate and 4.7 g (0.05 mol) of 98% 2-methylpyridine in 40 ml of toluene. The mixture is allowed to come to room temperature and stirred for a further 30 min. After 50 ml of water have been added, the phases are separated, the aqueous phase is extracted with 50 ml of toluene and the combined organic phases are washed with 50 ml of water. The toluene phase is dried by incipient distillation and used in the next stage (cf. Example 11).

The product can be isolated by distilling off the toluene. 10.4 g (95% strength, 82.3% of theory) of methyl 2-(dichloroacetyl)-3-(dimethylamino)acrylate are obtained.

Example 11

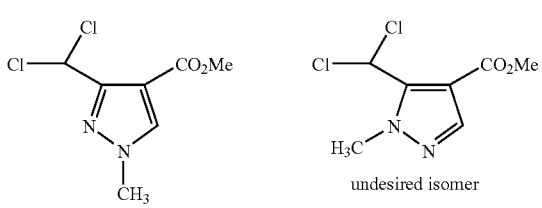

undesired isomer

A solution of 15.2 g (0.06 mol) of methyl 2-(dichloroacetyl)-3-(dimethylamino)acrylate in 60 ml of toluene is added dropwise with stirring and under protective gas at −50° C. within 45 min to 2.8 g (0.06 mol) of methylhydrazine in 60 ml of toluene. The mixture is stirred at −50° C. for 30 min, allowed to come to room temperature and stirred for another 2 h. After 60 ml of water have been added, the phases are separated, the aqueous phase is extracted with 30 ml of toluene, and the organic phases are combined and washed with 30 ml of water.

After the toluene has been distilled off, 12.6 g (83% of theory) of methyl 3-(dichloromethyl)-1-methyl-1H-pyrazole-4-carboxylate are obtained in a mixture with the undesired isomer [methyl 5-(dichloromethyl)-1-methyl-1H-pyrazole-4-carboxylate] in a ratio of 93.8:6.2 (GC-MS analysis).

The product can be recrystallized from diisopropyl ether (m.p. 115° C.).

Example 12

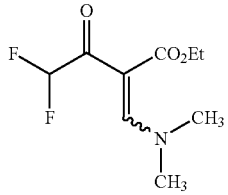

32.5 g of ethyl dimethylaminoacrylate in 200 ml of toluene are added dropwise with stirring and under protective gas at 0° C. to 26 g of difluoroacetyl chloride in 200 ml of toluene. Subsequently, 90.85 g of 10% sodium hydroxide solution are added dropwise. The mixture is stirred at 0° C. for 3 h and allowed to come to room temperature. The phases are separated. The aqueous phase is extracted with 80 ml of toluene and the combined organic phases are washed with 80 ml of water. The toluene phase is dried by incipient distillation and used in the next stage (see Example 11).

The product can be isolated by distilling off the toluene. 37.2 g (74% of theory) of ethyl 2-(difluoroacetyl)-3-(dimethylamino)acrylate are obtained.

$^1$H NMR(CD$_3$CN): δ=7.88 (s, 1H), 6.47, 6.61 and 6.74 (t, 1H), 4.13-4.19 (m, 2H), 3.32 (s, 3H), 2.85 (s, 3H), 1.25-1.28 (t, 3H) ppm.

Example 13

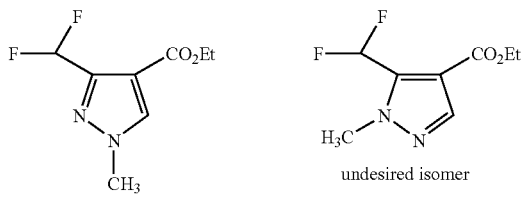

undesired isomer

A solution of 125.3 g of ethyl 2-(difluoroacetyl)-3-(dimethylamino)acrylate in 400 ml of toluene is added dropwise with stirring and under protective gas at −20° C. within 45 min to 31.2 g of methylhydrazine in 600 ml of toluene. The mixture is stirred at 0° C. for 3 h, allowed to come to room temperature and stirred at 20-25° C. for another 2 h. After 500 ml of water have been added, the toluene phase is removed and the water phase extracted twice more with 100 ml each time of toluene. The combined toluene phases are washed with 300 ml of water and incipiently distilled.

Ethyl 3-(difluoromethyl)-1-methyl-1H-pyrazole-4-carboxylate (yield 89.7% of theory) is obtained in a mixture with the undesired isomer [ethyl 5-(difluoromethyl)-1-methyl-1H-pyrazole-4-carboxylate] in a ratio of 89.2:10.8 (GC-MS analysis).

Example 14

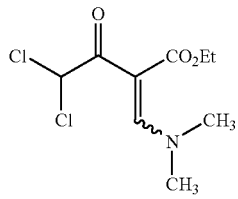

30.4 g (0.2 mol) of dichloroacetyl chloride in 50 ml of toluene are added dropwise at room temperature within 15 minutes to a solution of 28.9 g (0.2 mol) of ethyl dimethylaminoacrylate and 24.7 g (0.2 mol) of 5-ethyl-2-methylpyridine in 150 ml of toluene. The resulting yellow suspension is stirred at the same temperature for 2 hours. After 200 ml of water have been added, the phases are separated, the aqueous phase is extracted with 50 ml of toluene and the combined organic phases are washed with 50 ml of water, dried, concentrated and "degassed" in high vacuum.

47.6 g (92.1% of theory) of ethyl 2-(dichloroacetyl)-3-(dimethylamino)acrylate (m.p. 73° C.) are obtained.

Comparative Example 1 (Analogous to Example from U.S. Pat. No. 5,498,624, Columns 4 and 5)

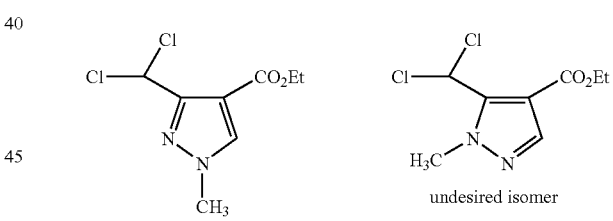

undesired isomer

A solution of 1.3 g (0.028 mol) of methylhydrazine in 5 ml of ethanol (absolute) is added dropwise under protective gas and with stirring at 0° C. within 40 min to 7.1 g (0.028 mol) of ethyl 2-dichloroacetyl-3-(dimethylamino)acrylate in 35 ml of ethanol (absolute). The mixture is heated to reflux for 2 h, allowed to come to room temperature, and the solution is stirred for another 2 h. After the ethanol has been distilled off, 50 ml of water and 50 ml of dichloromethane are added, the phases are separated, the aqueous phase is extracted with 30 ml of dichloromethane, and the organic phases are combined and washed with 30 ml of water.

After the dichloromethane has been distilled off, 6.5 g (37.5% of theory) of ethyl 3-(dichloro-methyl)-1-methyl-1H-pyrazole-4-carboxylate are obtained in a mixture with the undesired isomer in a ratio of 40.3:59.7.

Comparative Example 2 (Analogous to Example 3 from WO 03/051820)

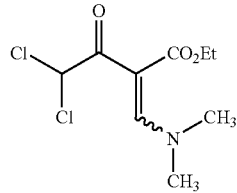

A solution of 16.2 g (0.11 mol) of dichloroacetyl chloride in 25 ml of toluene is added dropwise with stirring at −10° to −5° C. to 14.3 g (0.1 mol) of ethyl dimethylaminoacrylate and 11.1 g (0.11 mol) of triethylamine in 75 ml of toluene, and the mixture is subsequently heated to 50° C. After 100 ml of water have been added, the phases are separated, the aqueous phase is extracted with 50 ml of toluene and the combined organic phases are washed with 50 ml of water.

After the toluene has been distilled off, 23.7 g of a dark oil are obtained which contains 47.8% ethyl 2-(dichloroacetyl)-3-(dimethylamino)acrylate (corresponds to a theoretical yield of 44.6%).

Comparative Example 3 (Analogous to Example 4 of WO 03/051820)

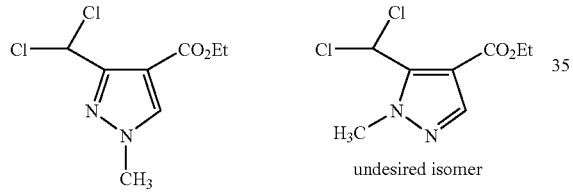

undesired isomer

A solution of 2.3 g (0.05 mol) of methylhydrazine in 10 ml of toluene was added dropwise at 0° C. to 12.7 g (0.05 mol) of ethyl 2-(dichloroacetyl)-3-(dimethylamino)acrylate in 50 ml of toluene. Subsequently, the mixture was left to stir for another 1 h. The toluene was distilled off under reduced pressure (<100 mbar) and temperatures of max. 45° C. The product did not crystallize with water. Extraction was effected twice with dichloromethane, and the combined organic phases were washed with water and concentrated.

11.1 g of ethyl 3-(dichloromethyl)-1-methyl-1H-pyrazole-4-carboxylate were obtained as a red oil in a mixture with the undesired isomers [ethyl 5-(dichloromethyl)-1-methyl-1H-pyrazole-4-carboxylate] in a ratio of 67.9:32.1 (GC-MS analysis).

The invention claimed is:

1. A process for preparing 2-dihaloacyl-3-aminoacrylic esters of formula (I)

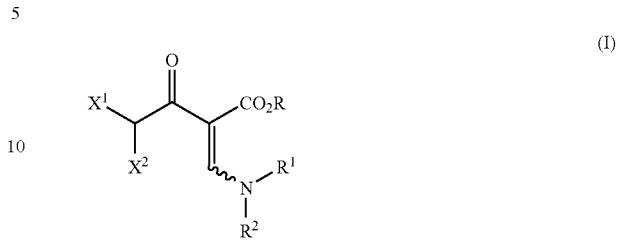

in which

R, $R^1$, and $R^2$ are each independently $C_1$-$C_4$-alkyl, and $X^1$ and $X^2$ are each independently fluorine, chlorine, or bromine, comprising reacting an acid halide of formula (II)

in which

Hal is fluorine, chlorine, or bromine, and $X^1$ and $X^2$ are each independently fluorine, chlorine, or bromine, with a dialkylaminoacrylic ester of formula (III)

in which R, $R^1$, and $R^2$ are each as defined for formula (I), in a water-immiscible organic solvent in the presence of a base, wherein the base is an inorganic aqueous base, pyridine, or a pyridine derivative.

2. A process according to claim 1 wherein the base is pyridine, picoline, 2-methyl-5-ethylpyridine, 2,4,6-collidine, quinoline, or quinaldine.

* * * * *